United States Patent [19]
Etienne

[11] Patent Number: 5,455,805
[45] Date of Patent: Oct. 3, 1995

[54] ULTRASONIC MEASURING APPARATUS HAVING ADJUSTABLE GAIN CONTROL

[75] Inventor: Jean-Daniel Etienne, Les Geneveys, Switzerland

[73] Assignee: Asulab S.A., Bienne, Switzerland

[21] Appl. No.: 164,543

[22] Filed: Dec. 10, 1993

[30] Foreign Application Priority Data

Dec. 29, 1992 [FR] France .................................. 92 15987

[51] Int. Cl.$^6$ .......................... G01S 15/00; G01N 29/00; A61B 8/00
[52] U.S. Cl. ................................ 367/98; 367/900; 73/631
[58] Field of Search ................ 367/98, 900; 128/660.07; 73/631

[56] References Cited

U.S. PATENT DOCUMENTS

| | | | |
|---|---|---|---|
| 3,309,914 | 3/1967 | Weighart | 73/631 |
| 3,367,173 | 2/1968 | Uphoff | 73/631 |
| 3,683,324 | 8/1972 | Hoxsie | 367/900 |
| 4,008,713 | 2/1977 | Griffith et al. | 128/2.05 Z |
| 4,420,824 | 12/1983 | Weber | 367/98 |
| 4,445,379 | 5/1984 | Yamaguchi et al. | 73/631 |
| 4,451,797 | 5/1984 | Bains, Jr. | 330/134 |
| 4,578,997 | 4/1986 | Soltz | 73/631 |
| 4,852,576 | 8/1989 | Inbar et al. | 128/660.6 |

FOREIGN PATENT DOCUMENTS

| | | |
|---|---|---|
| 0337297 | 4/1989 | European Pat. Off. . |
| 0356629 | 6/1989 | European Pat. Off. . |
| 9092346 | 3/1990 | WIPO . |

*Primary Examiner*—Ian J. Lobo
*Attorney, Agent, or Firm*—Griffin, Butler, Whisenhunt & Kurtossy

[57] ABSTRACT

In an ultrasonic measuring apparatus for emitting an ultrasonic pulse, receiving reflected echos and producing an echo signal representative of the echos resulting from each impulse, each echo signal has a first portion corresponding to echos from one group of interfaces and a second portion corresponding to echos from another group of interfaces. The apparatus comprises a gain control (24) for controlling the amplitude of each echo signal and a processor (26) for receiving and treating said echo signals. The processor treat a composite echo signal comprised of the first portion of a first echo signal combined with the second portion of a subsequent echo signal, the gain control setting the amplitude of both the first echo signal for the duration of the first echo signal and the amplitude of the subsequent echo signal at a second value for the duration of the subsequent echo signal, so as to optimize the amplitude of both the first portion of said first echo signal and the second portion of the subsequent echo signal in the composite echo signal when treated by processor.

13 Claims, 3 Drawing Sheets

ULTRASONIC MEASURING APPARATUS HAVING ADJUSTABLE GAIN CONTROL

FIELD OF THE INVENTION

The present invention relates generally to ultrasonic measuring apparatus comprising a probe for emitting an ultrasonic pulse at a predetermined repetition frequency and receiving echos reflected from a plurality of interfaces, an emitter circuit for controlling the emission of said ultrasonic pulses, a receiver circuit for producing an echo signal representative of the echos produced by each pulse, gain control means for controlling the amplitude of the echo signals, and processing means for receiving and treating the echo signals.

The invention is suitable for use in medical applications, and may be used, for example, in ultrasonic measuring apparatus which follow the temporal movement of the position the anterior and posterior walls of a blood vessel so as to determine the changes in the inner diameter and in the thickness of the walls of the blood vessel with time. Whilst it will be convenient to disclose the invention in relation to that exemplary application, it is to be appreciated that the invention is not limited to that application. The invention may, for example, be used in the measurement of the thickness of the corneal lens or in the non-invasive measurement of other bodily organs. The invention may also be used in non-medical applications requiring the measurement of wall thicknesses and/or inner diameters, such as in the non-destructive testing of pipes.

BACKGROUND OF THE INVENTION

FIG. 1 represents schematically a known manner of measuring the position of the walls of a blood vessel. This figure shows an ultrasonic transducer 1 placed above the skin 2 of a subject, which transducer 1 faces an artery 3 displayed in cross-section. The transducer 1 is controlled by an electronic circuit so as to emit an ultrasonic pulse 4, to receive ultrasonic echos resulting from the reflection of that pulse on the artery-tissue and artery-blood interfaces, and to create an echo signal in response thereto. Depending on the frequency of the ultrasonic transducer, this echo signal can represent four distinct echos 5, 6, 7 and 8, or only two echos corresponding respectively to a combination of the echos 5 and 6, and to a combination of the echos 7 and 8.

The movement of each interface is determined in the following manner. The transducer 1 emits a pulse 4 with a repetition frequency of generally between 10 Hz and 5 kHz. In order to follow the position of the echos, which are detected by the transducer after a delay which depends on the position of each interface, a temporal window of fixed size is used to define a time interval in which the echos are awaited, and which is adjusted, after each cycle, so that the echos would be detected in the centre of that window if the interfaces were immobile.

Knowledge of the temporal position of each interface as well as the propogation speed of the pulse in the blood and the tissue makes it possible, by measuring the interval, to determine the change of the inner diameter and the thickness of the anterior and posterior walls of the blood vessel 3 with time.

FIG. 1 is a schematic diagram only. In practice, the echos resulting from reflection of an impulse on the anterior and posterior walls of the blood vessel 3 are not as pure, but have a much more complex form as is shown by the elemental echos $E_{ant}$ and $E_{post}$ in FIG. 2. This deformation results from the fact that the ultrasonic pulse traverses tissues having different characteristics and from the fact that the interface between the wall of a blood vessel and the surrounding tissue is not as clearly defined as, for example, the interface between a metal plate and the surrounding air.

The position of the interfaces causing these echos, notably in the medical domain, thus cannot be directly and automatically determined from the form of the echo signal.

Several techniques may be used for detecting the position of the moving interfaces.

According to a first technique, the position of the interfaces is manually determined. The user displays the echo signal on an oscilloscope or another display means and choses a particular point on the echo signal onto which the echo tracker must lock. A second technique consists of processing the echo signal so as to suppress the noise, only keeping the part of the signal resulting from the reflection of the ultrasonic signal on each interface. In this technique the echo signals to be studied are firstly digitized and stored in real time, and then subsequently treated.

Swiss patent application no. 2871/91 describes a third technique in which an ultrasonic measuring apparatus emits a first ultrasonic pulse towards a blood vessel, converts the echo signal created from the echos detected by the transducer into a series of digital values (created during the opening of the temporal window) which are then stored. In an initialisation stage, these stored digital values are treated so as to select a reference point in each elemental echo of the echo signal, determine for each elemental echo the temporal position of each interface producing that elemental echo, and calculate for each elemental echo the temporal interval between the position of the reference point of that elemental echo and the temporal position of the interface obtained by the processing.

In parallel with this treatment, an assimilation phase occurs in which the digital values resulting from the detection of echo signals from subsequent ultrasonic pulses are treated so as to track the temporal position of the reference points from each echo signal. There follows then an acquisition phase in which the temporal position of each interface corresponding to each elemental echo of echo signals resulting from ultrasonic pulses subsequent to the assimilation phase are followed and memorized. Finally, an exploitation stage occurs during which the data memorized in the acquisition phase is used to provide information to the user, such as displaying the diameter of the blood vessel as a function of time.

It can be seen that the accurate analysis of the form of each echo signal, and in particular the form of its elemental echos, is an important part of each of the above-described techniques.

As shown in FIG. 2, however, the accuracy of this analysis is impeded by the fact that the elemental echo $E_{post}$ usually has a smaller magnitude than that of the elemental echo $E_{ant}$. This results from the greater distance within the subject through which the portion of the ultrasonic pulse reaching the posterior wall of the blood vessel 3, and the echos resulting therefrom, must travel. These greater distances arise both because the posterior wall of the blood vessel 3 is further away from the transducer 1 than the anterior wall, and also because of errors in the alignment of the transducer 1 and the reflective surfaces of the blood vessel 3 which result in the echos therefrom not being reflected directly back to the transducer 1.

Accordingly, it is desirable to have a ultrasonic measuring system providing characteristics which may be set so as to optimize the amplitude of a first elemental echo, and that may be altered to an optimum condition for a second elemental echo.

U.S. Pat. No. 4,451,797 discloses an automatic gain controller for a pulsed system used in the non-destructive testing of pipe walls. In the ultrasonic inspection system described therein, a probe emits an ultrasonic pulse, and receives the resulting echos from the near and far surfaces of the pipe. An agc amplifier is connected to the probe and produces an echo signal representative of the echos received by the probe. Following the emission of the pulse, a first circuit is connected to the output of the agc amplifier. When the echo from the near wall of the pipe is received, the magnitude of the echo signal is compared to a reference voltage and the difference used to set the amplification of the agc amplifier. The amplitude of the part of the echo signal corresponding to the echo from the near wall is thus optimized.

After the receipt of the echo from the near wall but before the receipt of the echo from the far wall, a second circuit is connected to the output of the agc amplifier. When this latter echo is received by the probe, the magnitude of the echo signal is compared to a different reference voltage, the difference being used to set the amplification of the agc amplifier to a new level. The amplitude of the part of the echo signal corresponding to the echo from the far wall is thus also optimized.

In this automatic gain controller, the amplification of each echo signal (resulting from a single ultrasonic pulse) is adjusted between the receipt of the near wall echo and the far wall echo. In many applications, however, this type of gain adjustment is not possible, as is the case when the temporal movement of the position of the walls of a blood vessel is followed.

Due to the capacitive and inductive properties inherent in any gain control circuit, a certain settling time is required if the amplification of a signal is to be changed. It has been found experimentally that for many such amplifier circuits, a settling time of several μsec is required. Ultrasonic waves travel within a subject at a speed of approximately 1540 m/sec. Whilst a femoral or carotid artery can have a diameter of as much as 1 cm, other human arteries may be as small as 4 mm, so that in the latter case the elemental echos $E_{ant}$ and $E_{post}$ may only be separated by 5.2 μsec for a stationary artery. As a subject's arteries are not stationary, but in fact move between pulses from the transducer 1, the time between the calculated moment at which the transducer gain can be adjusted and the actual moment at which the echo from the posterior wall of the blood vessel 3 is received is actually less than this. It can thus be seen that using the above described gain control system, insufficient time is available between elemental echos within which to change the amplitude of the echo signal.

SUMMARY OF THE INVENTION

It is an object of the present invention to provide an ultrasonic measuring apparatus which alleviates or overcomes the disadvantages of the prior art.

With that object in mind, the present invention provides an ultrasonic measuring apparatus comprising a probe for emitting an ultrasonic pulse at a predetermined repetition frequency and receiving echos reflected from a plurality of groups of interfaces, an emitter circuit for controlling the emission of said ultrasonic pulses, a receiver circuit for producing an echo signal representative of said echos produced by each of said pulses, each of said echo signals having a first portion corresponding to echos from one group of interfaces and a second portion corresponding to echos from another group of interfaces, gain control means for controlling the amplitude of each of said echo signals, processing means for receiving and treating said echo signals, characterised in that said processing means is adapted to treat a composite echo signal comprised of the first portion of a first echo signal combined with the second portion of a subsequent echo signal, said gain control means being adapted to set the amplitude of said first echo signal at a first value for the duration of said first echo signal, and the amplitude of said subsequent echo signal at a second value for the duration of said subsequent echo signal, so as to optimize the amplitude of both the first portion of said first echo signal and the second portion of said subsequent echo signal in said composite echo signal when treated by said processing means.

The amplitude of the elemental echos $E_{ant}$ and $E_{post}$ may thus both be optimized, in such a way which allows sufficient settling time for the means controlling this amplitude.

The following description refers in more detail to the various features of the ultrasonic measuring apparatus of the present invention. In order to facilitate an understanding of the present invention, reference is made in the description to the accompanying drawings where the ultrasonic measuring apparatus is illustrated in a preferred embodiment. It is to be understood that the ultrasonic measuring apparatus of the present invention is not limited to the preferred embodiment as illustrated in the drawings.

DESCRIPTION OF PREFERRED EMBODIMENTS

Figure 1:
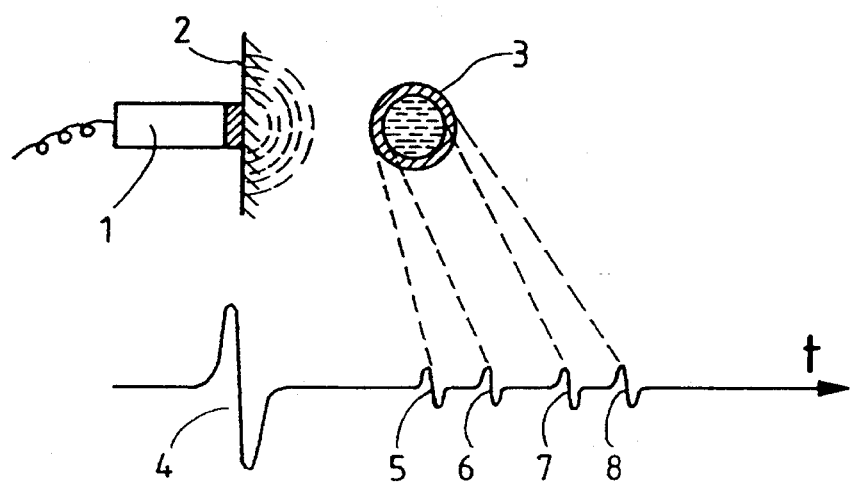
FIG. 1, already described, illustrates the principle of ultrasonic measurement of the position of the interfaces of the anterior and posterior walls of a blood vessel.
Figure 2:
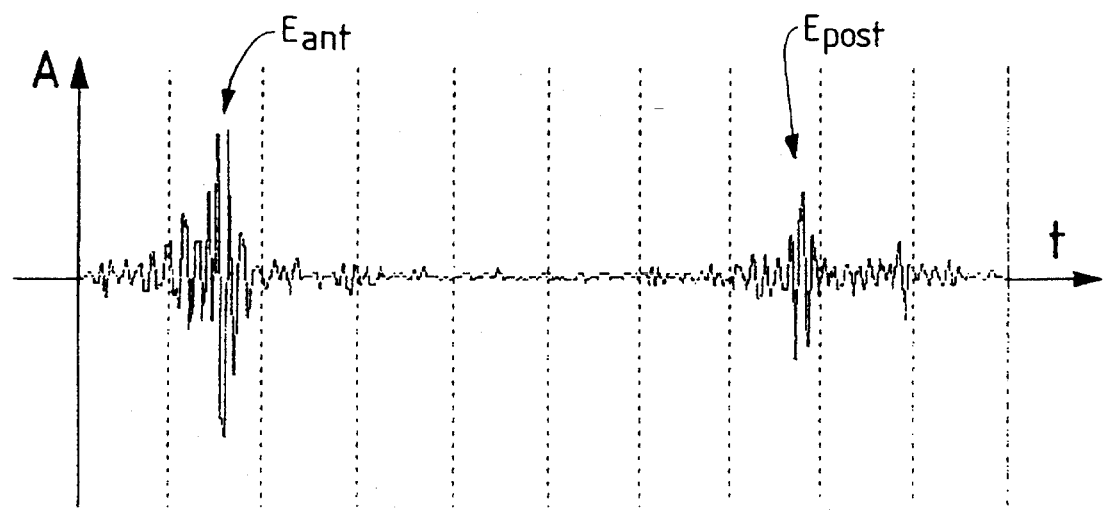
FIG. 2, already described, illustrates the temporal shape of an echo signal representing two elemental echos produced by the anterior and posterior walls of a blood vessel.
Figure 3:
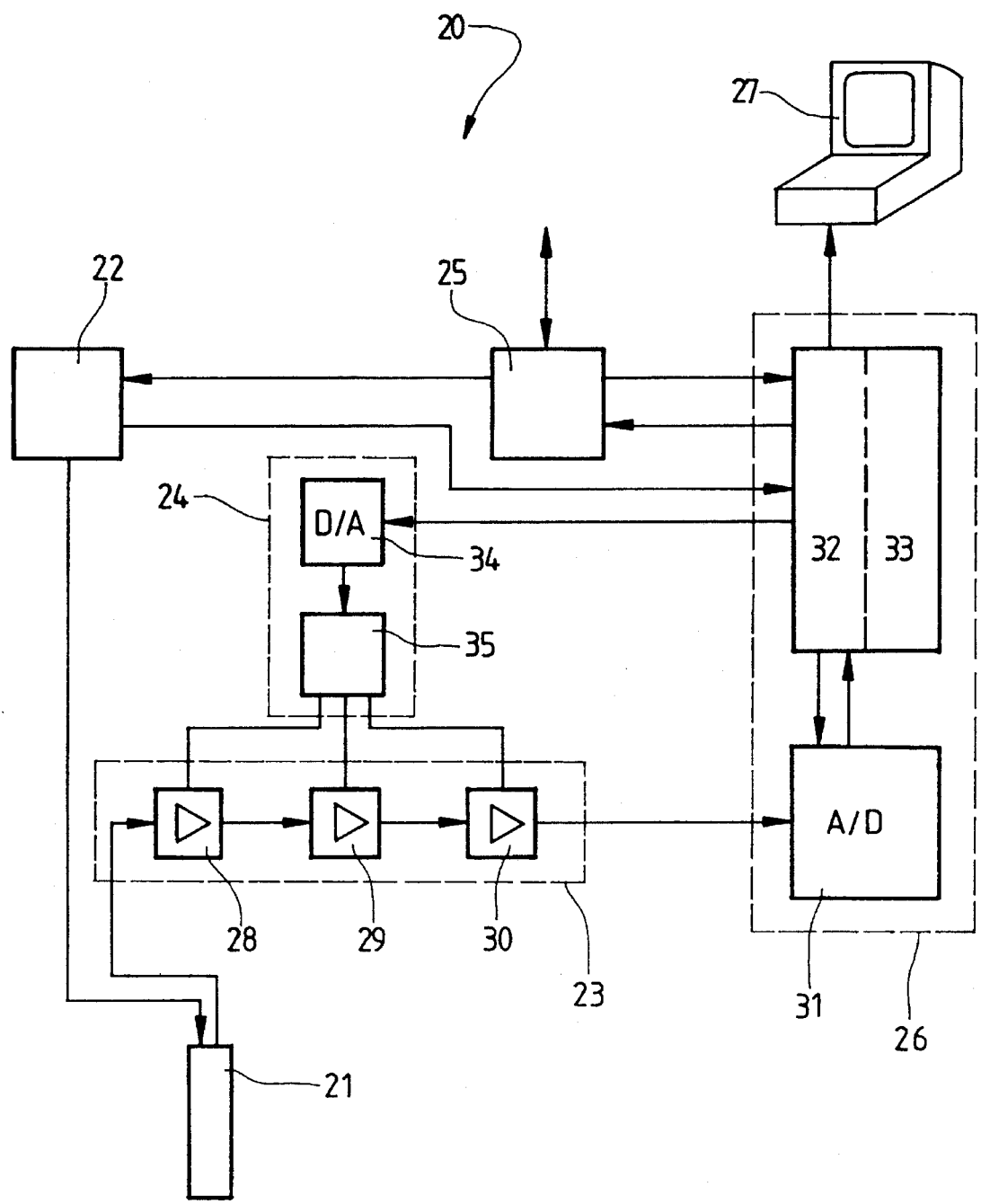
FIG. 3 shows diagramatically one embodiment of an ultrasonic measuring apparatus according to the present invention; and, FIG. 4 shows a schematic circuit diagram of one embodiment of the receiver circuit of the ultrasonic measuring apparatus of FIG. 3.

Referring now to FIG. 3 of the drawings, there is shown an ultrasonic measuring apparatus 20 comprising: a transducer having an ultrasonic probe 21, an emitter circuit 22, and a receiver circuit 23; a gain control circuit 24; an input/output circuit 25; processing means 26; and, display means 27. The ultrasonic probe 21 transmits an ultrasonic wave and receives echos resulting from the reflection of this ultrasonic wave.

The emitter circuit 22 delivers an electrical impulse which is transfromed by the probe 21 into a corresponding ultrasonic signal. The emitter circuit 22 also includes a clock (not shown) which provides a signal defining the frequency of repetition of the interrogation signal emitted by the probe 21. The central frequency of the ultrasonic impulse is chosen as a function of the intended application. It may be, for example, from 2 to 20 MHz.

The receiver circuit 23 receives the electrical signal delivered from the probe 21 corresponding to the ultrasonic echos received by the probe 21. The receiver circuit comprises three amplifier stages 28, 29 and 30 connected in cascade. A greater signal gain is thus obtained than with a single similar amplifier stage (although in other embodiments only one amplifier stage may be used). The electrical signal received from the probe 21 is amplified by each of the stages 28, 29 and 30 in turn and the resultant echo signal is received by the processing means 26.

The processing means 26 comprises an analog-digital converter 31, calculating means 32 and memory means 33. The echo signal delivered by the receiver circuit 23 is received by the analog-digital converter 31 and then supplied to the calculating means 32. The analog-digital converter may be a product of the type STR 8100 from SONIX Inc (Springfield, Va., USA) which is an analog-digital 8 bit converter capable of performing up to $10^8$ conversions/second. The calculating device 32 has an echo tracker which is used in a conventional manner to track the temporal position of each elemental echo of a group of elemental echos of the echo signal in relation to the ultrasonic signal transmitted. This position, that is ultimately the delay in each elemental echo signal from the ultrasonic impulse transmitted, varies with the distance between the ultrasonic probe and the mobile interface from which the ultrasonic pulse is reflected.

To carry out this tracking, the echo tracker receives a clock signal produced by the clock of the emitter circuit 22 and delivers to the analog-digital converter 31 a delay signal to start digitalization of the echo signal at a suitable moment. The echo tracker may be of the detection in extremum type (positive or negative) of the digitized echo signal. This extremum is not the correct value for assessing the movement of the mobile walls since the distance between two sampling points is equal to $c/(2.f)$ where $c=1540$ m/sec is the speed of the ultrasonic waves in the medium and the sampling frequency $f=50$ to 100 MHz. It is only possible to follow the displacement of the echo roughly.

Alternatively, the echo tracker may be of the crossover detection type such as described in EP-A-337 297 and EP-A-356 629.

The calculating means 32, which is advantageously a microprocessor of the 80×387 or 80×486 type, implements the measuring process of the apparatus 20 in conjunction with the memory means 33. As part of this process, the calculating means 32 sends a digital value to the gain control means 24, this digital value corresponding to the desired gain of the receiver circuit 23. The gain control means 24 comprises a digital-analog converter 34 and a gain signal circuit 35. The digital-analog converter 34 receives the digital value from the calculating means 32 and provides a corresponding analog signal to the gain signal circuit 35, which then provides appropriate signals to the gain control inputs of each of the amplifier stages 28, 29 and 30.

Various peripheral apparatus may also be added, such as the display means 27, the input/output circuit 25, and a printing means (not shown). The input/output circuit 25 allows a user to control the operation of the measuring apparatus 20 via, for example, a keyboard or other user input device. The input/output circuit 25 may also be connected to the clock of the emitter circuit 22 to control the frequency of repetition of the clock signal from the calculating means 32. It may also serve to synchronise other measuring equipment such as a sphygmanometer, a plethysmograph or a Doppler sensor in order to measure the blood pressure and blood velocity.

Figure 4:
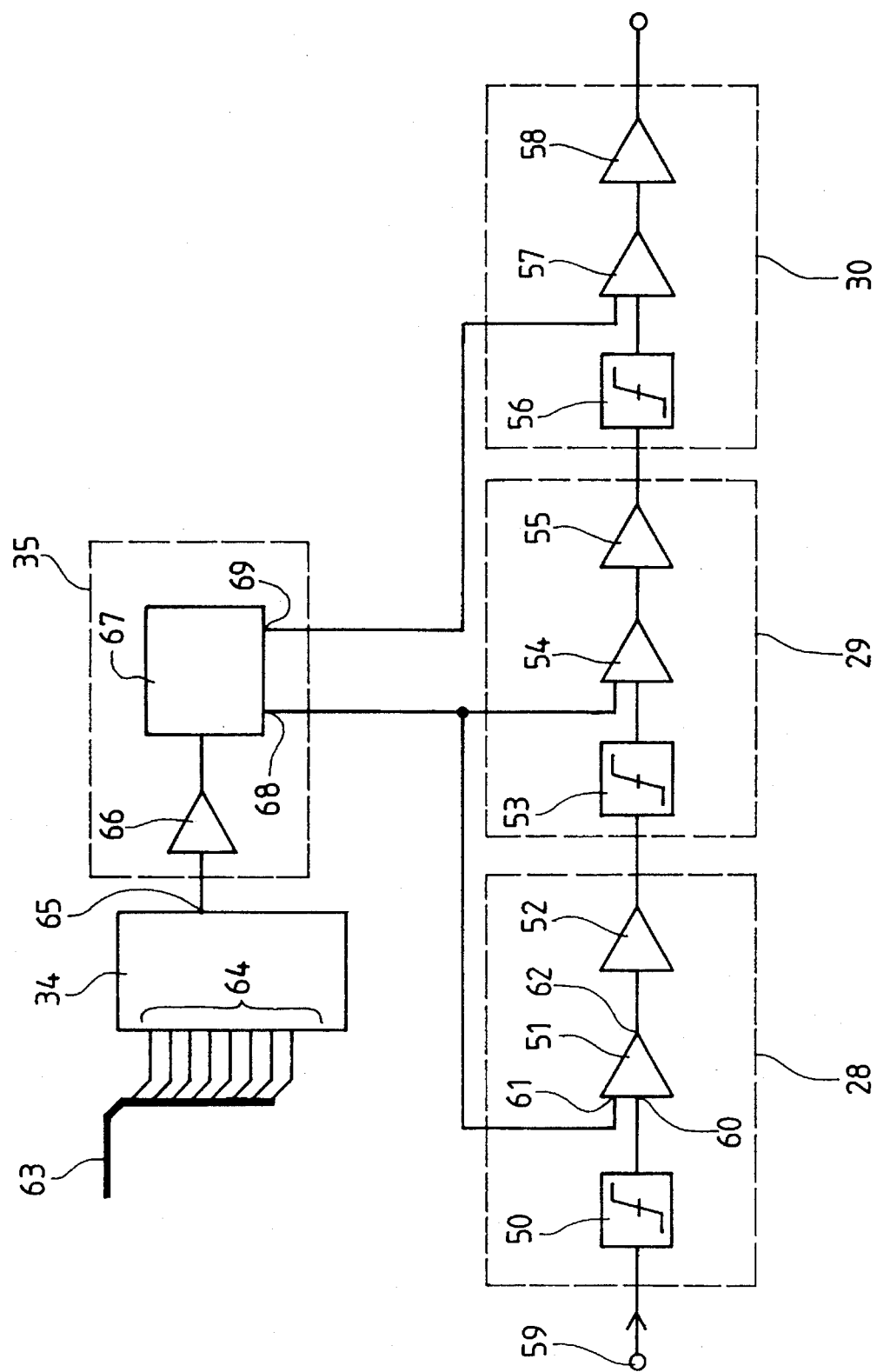

FIG. 4 shows a schematic circuit diagram of one embodiment of the receiver circuit 23 and the gain control means 24. The amplifier stage 28 comprises an amplitude limiter 50, a signal amplifier 51 and a voltage follower 52. Similarly, the amplifier stage 29 comprises an amplitude limiter 53, a signal amplifier 54 and a voltage follower 55, whilst the amplifier stage 30 comprises an amplitude limiter 56, a signal amplifier 57 and a voltage follower 58.

The electrical signal from the probe 21 is received at a terminal 59 of the amplifier stage 28 and passed to a signal input 60 of the amplifier 51. The limiter 50 protects the amplifier 51 by clipping the electrical signal supplied to the input 60 if its amplitude exceeds a predetermined limit. The amplifier 51 also has a gain input 61 for setting the amplification level of the signal received at its signal input 60.

The amplifier 51 has it output 62 connected to the voltage follower 52, in order to match the high-impedance output of the amplifier 51 to the low-impedance input of the next amplifier stage 29. The output of the voltage follower 52 is connected to the input of the next amplifier stage 29, the output of which is connected to the input of the following amplifier stage 30. The amplifier stages 29 and 30 are functionally identical to the first amplifier stage 28 and so their operation will not be described here in detail.

Each of the amplifiers 54 and 57 has a gain input, which like the gain input 61 of the amplifier 51 in the amplifier stage 28, determines the amplification level of the signal at its signal input. These gain inputs are provided by the digital-analog converter 34 via the gain signal circuit 35. The calculating means 32 provides a digital value to the digital-analog converter 34 on an 8 bit data bus 63. This digital value corresponds to the desired gain of the receiver circuit 23, and it is received by the digital analog circuit at its inputs 64. The digital value is converted to a corresponding analog voltage at its output 65.

The gain signal circuit 35 comprises an operational amplifier 66 and a voltage divider circuit 67. The operational amplifier 66 is configured, in a known way, as a voltage follower and so the voltage at its output is the same as that appearing at the output 65 of the digital-analog converter 34. The voltage divider circuit 67 has two outputs 68 and 69, the former of which supplies a gain signal to the gain input of both of the amplifiers 51 and 54, whilst the latter supplies a gain signal to the gain input of the amplifier 57.

The transfer characteristics of the voltage divider circuit 35 are different with respect to its output 68 and its output 69. When a low level signal is supplied to the amplifier 66, indicating that only a low level of amplification is to be given to the signal at the terminal 59, the output 69 provides a gain signal of an appropriate level to the amplifier 57 whilst the output 68 provides only a minimal gain signal to the amplifiers 51 and 54. As the signal at the terminal 59 is principally amplified by the amplifier 57, the Total Harmonic Distortion of the signal from the two previous amplifier stages, and thus the receiver circuit as a whole, is limited.

The gain signal from the output 69 increases with the required level of signal amplification until this latter can no longer be provided by the amplifier stage 30 alone. When a higher level of amplification is needed, the voltage divider circuit 67 causes the level of the gain signal from the output 68 to increase. The amplification of the signal by the amplifiers 51 and 54 is thus boosted so as to provide, in combination with the amplifier 57, the appropriate level of signal amplification.

The operation of the ultrasonic measuring apparatus 20 to determine the temporal inner diameter and wall thickness of the blood vessel 3 will now be described.

Before beginning measurements per se, the user selects the parameters of the apparatus, such as the repetition frequency and the sensor type, i.e. the central frequency of the ultrasonic pulse. These parameters may be selected via a keyboard connected to the input/output circuit 25, or automatically by the processing means 30 as a function of the application chosen by the user. By way of example, in the event of measuring the internal diameter and the thickness of the blood vessel wall, the repetition frequency is in the order of 10 Hz to 5 kHz for the measurement of the carotid artery. The duration of the delay transmitted to the analog-digital converter 26 is also adjusted, either manually or automatically, so that the elemental echos of the echo signals may be placed within the temporal window and each echo is correctly tracked by the echo tracker.

The display means 27 may be used to assist the user in the selection of these parameters. By adjusting the timing of the delay signal sent to the analog-digital converter 31 to start digitizing the echo signal, a trace of the (digitised) elemental echos $E_{ant}$ and $E_{post}$ may be displayed to the user to help correctly position the ultrasonic probe 21 with respect to the blood vessel 3.

In order to optimize the amplitude of both of the elemental echos received by the processing means 26, the calculating means 32 places a selected digital value on the bus 63 to the digital-analog converter 34. This digital value, which corresponds to an optimized amplitude of the first elemental echo $E_{ant}$, is converted into an analog voltage and used by the gain signal circuit 35 to adjust the gain of each of the amplifier stages 28, 29 and 30. Following the emission of an ultrasonic pulse from the probe 21, the calculating means 32 causes the analog-digital converter 31, after a selected delay, to commence digitizing the echo signal. The calculating means 32 treats each digital value of the digitized echo signal, including temporarily storing it in the memory means 33, until a chosen point between the two elemental echos $E_{ant}$ and $E_{post}$.

Between the time corresponding to this point and the emission of a subsequent ultrasonic impulse, and preferrably the next ultrasonic impulse from the probe 21, the calculating means 32 places another digital value on the data bus 63. This digital value corresponds to an optimized value of the amplitude of the second elemental echo $E_{post}$. As above, the analog-digital converter 31 commences digitizing the echo signal resulting from this subsequent ultrasonic pulse after the selected delay. However, the analog signal from the output of the receiver circuit 23 has an amplitude which is now optimized with respect to the second elemental echo $E_{post}$. The calculating means 32, at or after the time corresponding to the point chosen on the first echo signal above, treats the digital values of this second echo signal.

In summary, the amplitude of the elemental echo $E_{ant}$ is optimized in a first echo signal. The amplitude of the elemental echo $E_{post}$ is then optimized in a second echo signal. A portion of the first echo signal containing the elemental echo $E_{ant}$, and a portion of the second elemental echo signal $E_{post}$, are treated by the calculating means. In this way, a "composite" echo signal is effectively created in which the amplitude of both elemental echos is optimized.

The point at which the calculating means 32 ceases treatment of the first echo signal, and the point at which it begins treatment of the second echo signal, may be chosen by the user. Conveniently, the composite echo signal is shown to the user by the display means 27 to enable to appropriate selection of these points. The gain of the first and second echo signals may also be selected in this way. In other embodiments, however, this chosen point and these echo signal gains may be automatically selected by the calculating means 32.

It will be appreciated that variations to the foregoing may be used to realise the present invention. For example, the analog-digital converter 31 may be caused to digitize only a selected portion of the first echo signal containing the elemental echo $E_{ant}$, and another selected portion of the second echo signal containing the elemental echo $E_{post}$.

In addition, the calculating means 32 may be adapted to treat all of the digital values from both the first and second echo signals. For example, both the first and second echo signals may be displayed together by the display means 27. This would, however, use more memory locations in the memory means 33 than necessary and may result in confusion to the user.

In another embodiment, the amplitude of the echo signals may be varied by adjusting the amplitude of the ultrasonic pulses emitted from the probe 22. Such a solution may not be desirable in medical applications though, as the more powerful pulse may cause internal damage to a subject.

The user can then proceed to measure the position of the interfaces of the blood vessel by using the apparatus 20 to carry out the measuring process described in Swiss patent application no. 2871/91. This measurement process will not be described here in detail, but can be divided into three stages, namely an initialisation stage, an assimilation stage and a processing stage. In the initialisation stage, the digital values transferred to and stored in the memory means 33 are treated so as to select a reference point in each elemental echo of the echo signal, determine for each elemental echo the temporal position of each interface producing that elemental echo, and calculate for each elemental echo the temporal interval between the position of the reference point of that elemental echo and the temporal position of the interface obtained by the processing.

In parallel with this treatment, the assimilation phase occurs in which the digital values resulting from the detection of echo signals from subsequent ultrasonic pulses are treated so as to track the temporal position of the reference points from each echo signal.

There follows then the acquisition phase in which the temporal position of each interface corresponding to each elemental echo of echo signals resulting from ultrasonic pulses subsequent to the assimilation phase are followed and memorized. Finally, an exploitation stage occurs during which the data memorized in the acquisition phase is used to provide information to the user, such as displaying the diameter of the blood vessel as a function of time.

As will be understood by those skilled in the art the present invention may be used in relation to the detection of other groups of echos (for which differing gains are needed to optimise their amplitudes) received from different interfaces, and is not restricted to applications concerning the elemental echos found in the detection of the echos from the walls of a blood vessel as described in the above embodiment.

Finally, it is to be understood that various modifications and/or additions may be made to the ultrasonic measuring apparatus without departing from the ambit of the present invention as defined in the claims appended hereto.

I claim:

1. Ultrasonic measuring apparatus comprising:
   a probe for emitting ultrasonic pulses at a predetermined repetition frequency and receiving echos reflected from a plurality of groups of interfaces, an emitter circuit for controlling the emission of said ultrasonic pulses, a receiver circuit for sequentially producing echo signals, each echo signal being representative of said echos produced by each of said pulses, each of said echo signals having a first portion corresponding to echos from one group of said interfaces and a second portion corresponding to echos from another group of said interfaces, gain control means for controlling the amplitude of each of said echo signals, processing means for receiving and treating said echo signals, characterised in that said processing means comprises means for treating a composite echo signal essentially consisting of the first portion of a first of the sequentially produced echo signals combined with the second portion of a subsequently produced echo signal, and in that said gain control means comprise means to set the gain of said first of the sequentially produced echo signals at a first value for the duration of said first of the sequentially produced echo signals, and the gain of said subsequently produced echo signal at a second value for the duration of said subsequently produced echo signal, so as to optimize the amplitude of both the first portion of said first of the sequentially produced echo signals and the second portion of said subsequently produced echo signal in a single composite echo signal treated by said processing means.

2. Ultrasonic measuring apparatus according to claim 1, characterised in that said receiver circuit comprises an amplifier circuit having an adjustable gain, said adjustable gain being controlled by said gain control means.

3. Ultrasonic measuring apparatus according to claim 2, characterised in that said amplifier circuit comprises a plurality of amplifier stages connected in cascade.

4. Ultrasonic measuring apparatus according to claim 3, characterised in that one or more of said amplifier stages comprises an amplifier each having a signal input, an input for setting said adjustable gain and an output, each said input being connected to said gain control means.

5. Ultrasonic measuring apparatus according to claim 4, characterised in that each of said one or more amplifier stages further comprises a limiter connected to its signal input, and a voltage follower connected to its output.

6. Ultrasonic measuring apparatus according to claim 1 characterised in that said gain control means comprises a digital-analog converter, and a gain signal supply, said digital-analog converter receiving from said processing means a digital value representing a selected echo signal amplitude, and supplying to said gain signal supply an analog signal corresponding to said selected amplitude.

7. Ultrasonic measuring apparatus according to claim 6, characterised in that said gain signal supply has a first output for supplying one or more earlier stages of said amplifier stages and a second output for supplying one or more later stages of said amplifier stages, said second output supplying a greater gain signal than said first output at low levels of echo signal amplification so as to reduce the harmonic distortion of said receiver circuit.

8. Ultrasonic measuring apparatus according to claim 6, characterised in that said processing means comprises an analog-digital converter for digitizing said echo signals into digital values, and calculating means for manipulating said digital values.

9. Ultrasonic measuring apparatus according to claim 5, characterised in that said gain control means comprises a digital-analog converter, and a gain signal supply, said digital-analog converter receiving from said processing means a digital value representing a selected echo signal amplitude, and supplying to said gain signal supply an analog signal corresponding to said selected amplitude.

10. Ultrasonic measuring apparatus according to claim 9, characterised in that said gain signal supply has a first output for supplying one or more earlier stages of said amplifier stages and a second output for supplying one or more later stages of said amplifier stages, said second output supplying a greater gain signal than said first output at low levels of echo signal amplification so as to reduce the harmonic distortion of said receiver circuit.

11. Ultrasonic measuring apparatus according to claim 7, characterised in that said processing means comprises an analog-digital converter for digitizing said echo signals into digital values, and calculating means for manipulating said digital values.

12. Ultrasonic measuring apparatus according to claim 9, characterised in that said processing means comprises an analog-digital converter for digitizing said echo signals into digital values, and calculating means for manipulating said digital values.

13. Ultrasonic measuring apparatus according to claim 10, characterised in that said processing means comprises an analog-digital converter for digitizing said echo signals into digital values, and calculating means for manipulating said digital values.

* * * * *